(12) United States Patent
Takesako et al.

(10) Patent No.: US 6,235,912 B1
(45) Date of Patent: May 22, 2001

(54) SPHINGOSINE ANALOGUES (75) Inventors: Kazutoh Takesako, Otsu; Toru Kurome; Naoyuki Awazu, both of Kusatsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/380,647

(22) PCT Filed: Mar. 12, 1998

(86) PCT No.: PCT/JP98/01038

§ 371 Date: Oct. 15, 1999

§ 102(e) Date: Oct. 15, 1999

(87) PCT Pub. No.: WO98/40349

PCT Pub. Date: Sep. 17, 1998

(30) Foreign Application Priority Data

Mar. 12, 1997 (JP) .................................................. 9-079094
Sep. 11, 1997 (JP) .................................................. 9-267969

(51) Int. Cl.[7] ...................... C07C 231/00; C07C 233/00; C07C 235/00; C07C 237/00
(52) U.S. Cl. .................. 554/51; 554/56; 554/58; 554/59
(58) Field of Search ................ 554/51, 56, 58, 554/59

(56) References Cited

FOREIGN PATENT DOCUMENTS

| 0 897 988 A1 | 2/1999 | (EP) . |
| 62-138497 | 6/1987 | (JP) . |

OTHER PUBLICATIONS

Efficient synthesis of sphingosine–1–phosphonate and homo–sphingosine–1 phosphonate, vol. 7, Iss 5, p. 573–576, Mar. 1997.*

Tarnowski et al, Efficient Synthesis of Sphingosine–1–Phosphonate and Homo–Sphingosine–1–Phosphonate, *Bioorganic & Medicinal Chemistry Letters* 7 (5): 573–576, Mar. 4, 1997.

* cited by examiner

*Primary Examiner*—Johann Richter
*Assistant Examiner*—Diedra Faulkner
(74) *Attorney, Agent, or Firm*—Connolly, Bove, Lodge & Hutz, LLP.

(57) ABSTRACT

The present invention aims to provide a novel sphingosine analogue, which is useful as an intermediate for syntheses of novel lipid derivatives such as sphingolipid derivatives and the like that can regulate the effects of sphingolipid.

The present invention relates to a sphingosine analogue represented by the general formula (I) described below.

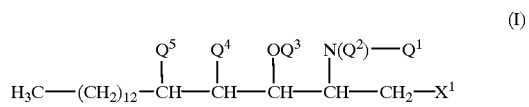

In the formula, as for $Q^1$, $Q^2$ and $Q^3$, $Q^1$ and $Q^2$, which are the same or different each other, are hydrogen, alkyl groups having 1–4 of carbon atoms, acyl groups having 2–5 of carbon atoms, or protecting groups of the amino group, and $Q^3$ is a hydrogen or a protecting group of the hydroxyl group; or $Q^2$ and $Q^3$ make up an isopropylidene group and $Q^1$ is a hydrogen or a protecting group of the amino group. $Q^4$ and $Q^5$, which are the same or different each other, are hydroxyl groups, acyl groups having 2–5 of carbon atoms, —O—$Q^6$, or hydrogen; or $Q^4$ and $Q^5$ make up a covalent bond. $Q^6$ is a protecting group of the hydroxyl group. $X^1$ is —COOH, —CONH$_2$, —CO—$Q^7$, —CH$_2$OH, or —CH$_2$O—$Q^8$. $Q^7$ is a protecting group of the carboxyl group, and $Q^8$ is a protecting group of the hydroxyl group.

1 Claim, 8 Drawing Sheets

SPHINGOSINE ANALOGUES

This application is a continuation of PCT/JP98/01038 Mar. 12, 1998.

TECHNICAL FIELD

The present invention relates to a novel sphingosine analogue, which is useful as an intermediate for syntheses of TKR1785's and their derivatives useful as drugs for the treatment of fungal infections, allergic diseases, etc., and also as an intermediate for syntheses of novel sphingolipid derivatives. The present invention also relates to a process for production of a novel sphingolipid.

PRIOR ART

Sphingosine is a compound having the chemical formula shown in the general formula described below, in which $Y^1$ is hydrogen. It is known that various sphingolipids having sphingosine as a constituent are widely distributed in the living body including on the surface of cell membranes of cells in the nervous system. Also we know glycosphingolipids binding one or several kinds of sugars as $Y^1$ via a glycoside bond to a ceramide having a fatty acid bound to the amino group of sphingosine via a peptide bond, and sphingophospholipids, including sphingomyelin, binding a phosphoric acid and a base such as choline or ethanolamine as $Y^1$ to the above-mentioned ceramide.

A sphingolipid is one of the lipids having important roles in the living body. We know a disease called lipidosis which is caused by accumulation of a specified sphingolipid in the body concomitant with the abnormalities in the metabolic pathways due to respiration deficiency and others. Attractive effects of sphingolipids present on the cell membranes include functions in the regulation of cell growth and discrimination of each cells; functions in the developments and differentiation; functions in nerves; involvement in the infections and malignancy of cells; and others. Lots of physiological roles of such effects remain to be solved. Recently a possibility that ceramide, a derivative of sphingosine, has an important role in the mechanism of cell signal transduction is indicated, and studies about its effects on apoptosis and cell cycle have been actively performed.

Fungi and plants have sphingolipids and the major sphingosine contained in these organisms has the formula described below. It is known that these lipids have important roles in the cell growth of fungi and plants, but details of the roles remain to be solved.

Recently it has been known that derivatives of sphingolipids and their related compounds exhibit a variety of biological activities through inhibition or activation of the metabolism pathways. These compounds include inhibitors of protein kinase C, inducers of apoptosis, immunosuppressive compounds, antifungal compounds, and the like. Substances having these biological activities are expected to be useful compounds for various diseases.

ABSTRACT OF THE INVENTION

The present invention intends to give a novel sphingosine analogue that is useful as an intermediate for synthesis of a novel lipid derivative, such as sphingolipid derivatives and the like, capable of controlling the function of sphingolipid.

In the course of a search for novel biologically active compounds, the inventors isolated lots of microorganisms, obtained biologically active compounds produced by the microorganisms, and studied on the biological properties. We discovered novel biologically active compounds TKR1785's, which were active against pathogenic fungi including Candida, Aspergillus, Cryptococcus and Malassezia in the culture broth of a strain belonging to Penicillium sp. The inventors also found that the TKR1785's inhibit enzymes involved in allergic reactions.

In this specification, TKR1785's are compounds shown in the following general formula (II). TKR1785's described above include TKR1785-I shown as the following formula (IIa) and TKR1785-II (IIb).

The inventors succeeded in preparation of novel sphingosine analogues represented by the following formula (III) by hydrolysis of TKR1785's described above. Furthermore they revealed that the compounds are useful intermediates for synthesis of TKR1785's.

(III)

Also, the inventors found that the group of compounds described in the following general formula (I), which includes the compound described in the above formula (III) as the representative, is useful to synthesize a novel biologically active compound including novel sphingolipid analogues or others, and then accomplished the present invention.

(I)

In the formula, as for $Q^1$, $Q^2$ and $Q^3$, $Q^1$ and $Q^2$, which are the same or different each other, are hydrogen, alkyl groups having 1–4 of carbon atoms, acyl groups having 2–5 of carbon atoms, or protecting groups of the amino group, and $Q^3$ is a hydrogen or a protecting group of the hydroxyl group; or $Q^2$ and $Q^3$ make up an isopropylidene group and $Q^1$ is a hydrogen or a protecting group of the amino group. $Q^4$ and $Q^5$, which are the same or different each other, are hydroxyl groups, acyl groups having 2–5 of carbon atoms, —O—$Q^6$, or hydrogen; or $Q^4$ and $Q^5$ make up a covalent bond. $Q^6$ is a protecting group of the hydroxyl group. $X^1$ is —COOH, —CONH$_2$, —CO—$Q^7$, —CH$_2$OH, or —CH$_2$O—$Q^8$. $Q^7$ is a protecting group of the carboxyl group, and $Q^8$ is a protecting group of the hydroxyl group.

DETAILED DESCRIPTION OF THE INVENTION

Following is the present invention now described in detail.

Sphingosine analogues of the present invention are represented by the general formula (I) described above. The above alkyl group having 1–4 of carbon atoms is not particularly restricted, but includes, for example, methyl, ethyl, propyl, i-propyl, n-butyl, t-butyl group, and the like.

The above acyl group having 2–5 of carbon atoms is not particularly restricted, and includes, for example, acetyl, propionyl, butyryl, valeryl group, and the like.

The protecting group of the above amino group is not particularly restricted, but includes, for example, t-butoxycarbonyl (Boc), trichloroethoxycarbonyl (Troc) group, and the like.

The protecting group of the above hydroxyl group is not particularly restricted, but includes, for example, benzyl (Bzl), acetyl, methyl, trimethylsilyl group, and the like.

$Q^7$ described above is a protecting group of the carboxyl group. The protecting group of the above carboxyl group is not particularly restricted, but includes, for example, a phenacyl (Pac) group, Bzl group, and the like.

$Q^6$ and $Q^8$ described above are protecting groups of the hydroxyl group. The protecting group of the above hydroxyl group is not particularly restricted, but includes, for example, those described above.

Sphingosine analogues described above are included in a compound represented by the general formula (I) described above and include, for example, the compounds shown in Table I described below.

The compound represented by the above formula (III), which is shown in Table 1 as the compound (1), can be converted to an acyl derivative of the hydroxyl or amino group by means of a conventional method using acid anhydride, acid chloride, or the like. The compound represented by the above formula (III) can be converted to an N-alkylated derivative of the amino group by using sodium hydride and alkyl iodide. In addition, the compound represented by the above formula (III) can be converted to an amide by methylation of the carboxyl group followed by ammonolysis, or to an alcohol by reduction using lithium alminium hydride (LiAlH$_4$), sodium borohydride (NaBH$_4$), or the like.

The compound represented by the above formula (III) can be converted to a compound shown by the general formula (I) except for the compound shown by the above formula (III) by means of a selective modification of a specified functional group selected from the hydroxyl, amino, or carboxyl group, which the compound represented by the above formula (III) has, through selective reaction or use of an appropriate protecting group. In this case, various protecting groups which are often used for the peptide synthesis can suitably be available. Such protecting groups include protecting groups of the amino group, protecting groups of the carboxyl group, or protecting groups of the hydroxyl group described above.

The protecting group described above is respectively removed in need by a corresponding known elimination reaction or its applied elimination reaction, and an objective compound is obtained. In the case that a protecting group that can be eliminated by a different condition is used, the elimination reaction carried out as described above can make easily a selective modification. For example, a selective modification of the amino group can be carried out by protection of the amino group by a Boc group, protection of the hydroxyl group by an acetyl group, protection of the carboxyl group by a methyl group, standing at an acidic condition to remove and eliminate the Boc group selectively, formation of a peptide bond with an organic acid, and alkali hydrolysis thereafter; and a compound in which only the amino group is modified selectively is obtained. If a compound having a hydroxyl group instead of the carboxyl group is used as a starting material and the hydroxyl group is protected by acyl group, a ceramide analogous compound can be obtained.

Among the compounds represented by the above general formula (I) of the present invention, the compound represented by the above formula (III) can be produced by hydrolysis of TKR1785's represented by the above general formula (II) such as TKR1785-I or TKR1785-II. For example, the composition can be obtained by treatment of TKR1785-I shown as the above formula (IIa) with acid hydrolysis, e.g. carrying out the decomposition under the condition of 6N HCl, at 110° C. for over night or the like which is used for the hydrolysis of the peptide bond, followed by neutralization of the reaction solution and being adjusted to alkali. The compound prepared is isolated by neutralization of the reaction solution again, extraction with an organic solvent such as chloroform, a mixture of chloroform/methanol or the like, and if necessary, further purification using an absorption chromatography using silica gel or a reversed phase partition chromatography using a chemical-bonded silica gel. The lactone represented by the below formula (IV) can be obtained when TKR1785-I is subjected to acid hydrolysis under the condition similar to that described above, concentration and purification. For example, this compound is available to introduce Boc groups to the amino group alone or both of the amino and hydroxyl groups by Boc derivatization. Alkali hydrolysis thereafter leads to synthesize one compound represented by the above general formula (I).

(IV)

Additionally, as to a compound in which $Q^4$ and $Q^5$ of the above general formula (I) are bound, including a compound represented by the above-mentioned formula (III), a compound having a double bond between carbon 5 and carbon 6, such as the compound (10) shown in Table 1 described below, can be easily obtained from the lactone shown above as the formula (IV) through dehydration by treatment with sulfuric acid or the reaction with thionyl chloride in pyridine, and following alkali hydrolysis. The compound having a hydroxyl group as $Q^4$ of the above general formula (I) can be obtained by direct introduction of a hydroxyl group to the obtained dehydration product of the above formula (IV) treating with concentrated sulfuric acid, or by alkali hydrolysis after its epoxidation by reduction.

TKR1785's described above, thus TKR1785-I and TKR1785-II, are prepared by culturing a strain producing TKR1785's and belonging to Penicillium sp., and isolating them from the cultured broth thereafter. The strain useful to produce TKR1785's described above is exemplified by Penicillium sp. TKR1785 (referred as "strain TKR1785" thereafter). That is, strain TKR1785 is inoculated into a nutrient medium and cultured in liquid to obtain TKR1785's described above.

The culture described above is carried out at 15 to 25° C. preferably, and the incubation for 3 to 11 days usually gives a sufficient production. TKR1785's accumulated in the cultured product are obtained by purification utilizing their physicochemical and biological properties. The purification described above includes a method using high performance liquid chromatography, in which a chemical-bonded silica gel including octadecyl, octyl, or phenyl group, a porus-polymer gel, or the like is used. The mobile phase includes an aqueous organic water-soluble solvent, for example, aqueous methanol, aqueous acetonitrile, or the like.

Sphingosine analogues of the present invention represented by the above general formula (I) are useful as intermediates of syntheses of TKR1785's or their derivatives. For example, the compound represented by the above formula (III) is able to be used as an intermediate of synthesis of TKR1785-I or its derivative. In order to prepare TKR1785-I or its derivative from the compound represented by the above formula (III), you can obtain it by synthesizing according to the scheme 1 shown later.

The compound represented by the above formula (I) is useful to use syntheses of various sphingolipid analogues as a sphingosine analogous lipid. For example, in order to prepare the compound represented by general formula (V) described below, which has —CH$_2$OH as $X^1$ and is similar to ceramide having a fatty acid such as a palmitic acid bound to the amino group via a peptide bond, it is needed that a starting material which has an amino group and three hydroxyl groups respectively protected by different protecting groups is used, and is selectively removing the protecting group of amino group, binding a fatty acid via a peptide bond, and removing the protecting group of hydroxyl groups. Additionally, the obtained compound (V) described below can be used to synthesize a sphingoglycolipid which has a monosaccharide such as galactose or glucose, or an oligosaccharide at the position of $Q^8$ of the compound shown as the above formula (I). In this case, if $Q^3{}_1$, $Q^5$, and $Q^8$ are protected by protecting groups which can be removed under different conditions, the protecting group of $Q^8$ is selectively removed to allow to use for synthesis of a sphingoglycolipid analogue.

(V)

In the formula, $Y^2$ is an acyl group of a fatty acid such as myristoyl (C14:0), palmitoyl (C16:0), stearoyl (C18:0), oleoyl (C18:1), or lignoceroyl (C24:0) group.

The sphingosine analogues of the present invention are immunosuppressive and toxic to tumor cells and have a medical use.

BEST MODE FOR CARRYING OUT THE INVENTION

The following examples illustrate the present invention in further detail but are not intended to define the scope of the invention.

REFERENCE EXAMPLE 1

Synthesis of TKR 1785-1 and TKR 1785-2

From a slant culture of TKR1785 strain (FERM BP-5788), a loop was taken to inoculate a 500 ml conical flask containing 100 ml of a liquid medium [Difco yeast nitrogen base 0.67% (w/v) and glucose 2.0% (w/v)] and cultured under shaking at 25° C. for 5 days to provide a seed culture. A 1.0 ml portion of this seed culture was inoculated into 18 conical flasks of 500 ml capacity each containing 125 ml of the above liquid medium and cultured under shaking (220 rpm) at 25° C. for 9 days. The resulting culture was centrifuged to separate a supernatant and a cellular fraction. The cellular fraction was well mixed and extracted with 1 L of methanol and the extract was concentrated under reduced pressure. The residue was diluted with 300 ml of water and, after sufficient mixing, adjusted to pH 2. Then, 300 ml of ethyl acetate was added and mixed thoroughly for washing with ethyl acetate. The aqueous layer was adjusted to pH 9 and extracted with 300 ml of ethyl acetate. The extract was concentrated under reduced pressure to provide 52 mg of a residue.

This residue was dissolved in 0.4 ml of methanol and subjected to high performance liquid chromatography to provide two antifungal fractions I and II. Those active fractions were respectively concentrated under reduced pressure to provide 16 mg of TKR1785-I and 3 mg of TKR1785-II both as white powders. The high performance liquid chromatography was carried out under the following conditions.

Apparatus: LC8A (Shimadzu)
Column: YMCpack C18 (2.0 cm×25 cm) (Y.M.C.)
Mobile phase: 0.05% trifluoroacetic acid-55% (v/v) acetonitrile/water
Physicochemical Properties JMS-DX302 Mass Spectrometer (Jeol Ltd.) was used for mass spectrometry. JNM-A500 Nuclear Magnetic Resonance Spectrometer (Jeol Ltd.) was used for $^1$H-NMR spectrometry (in deuterated dimethyl sulfoxide, reference: deuterated dimethyl sulfoxide) and $^{13}$C-NMR spectrometry (in deuterated dimethyl sulfoxide, reference: deuterated dimethyl sulfoxide). For ultraviolet absorption spectrometry (in methanol), UV-250 self-recording spectrophotometer (Shimadzu) was used. For infrared absorption spectrometry (KBr), 270-30 Infrared Spectrophotometer (Hitachi) was used. L-8500 (Hitachi) was used for amino acid analysis.

The physicochemical properties of TKR1785-I areas follows.

Figure 1:
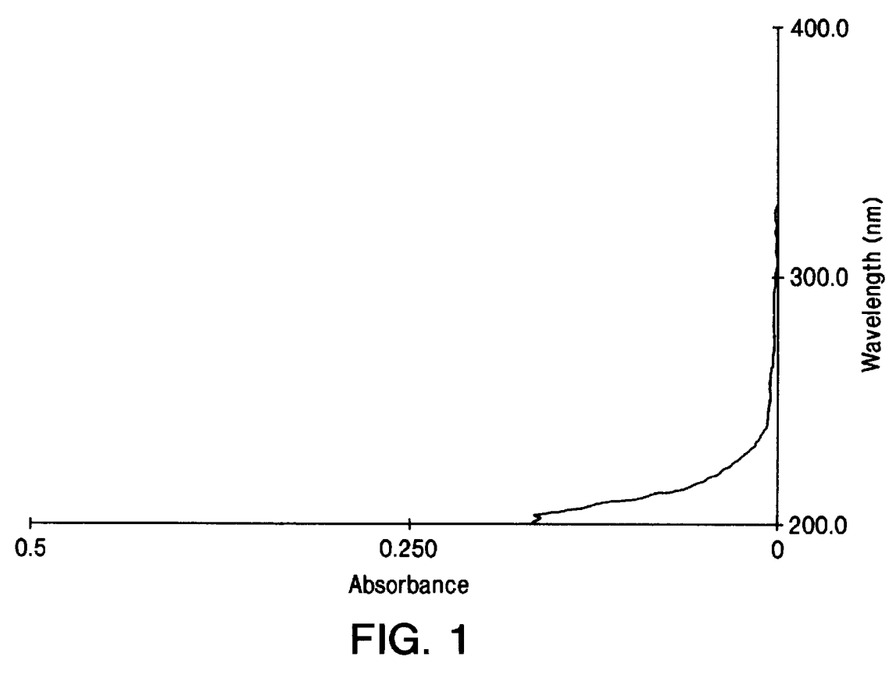
FIG. 1 is an ultraviolet absorption spectrum of the bioactive substance TKR1785-I. The ordinate represents wavelength (nm) and the abscissa represents absorbance.
Figure 3:
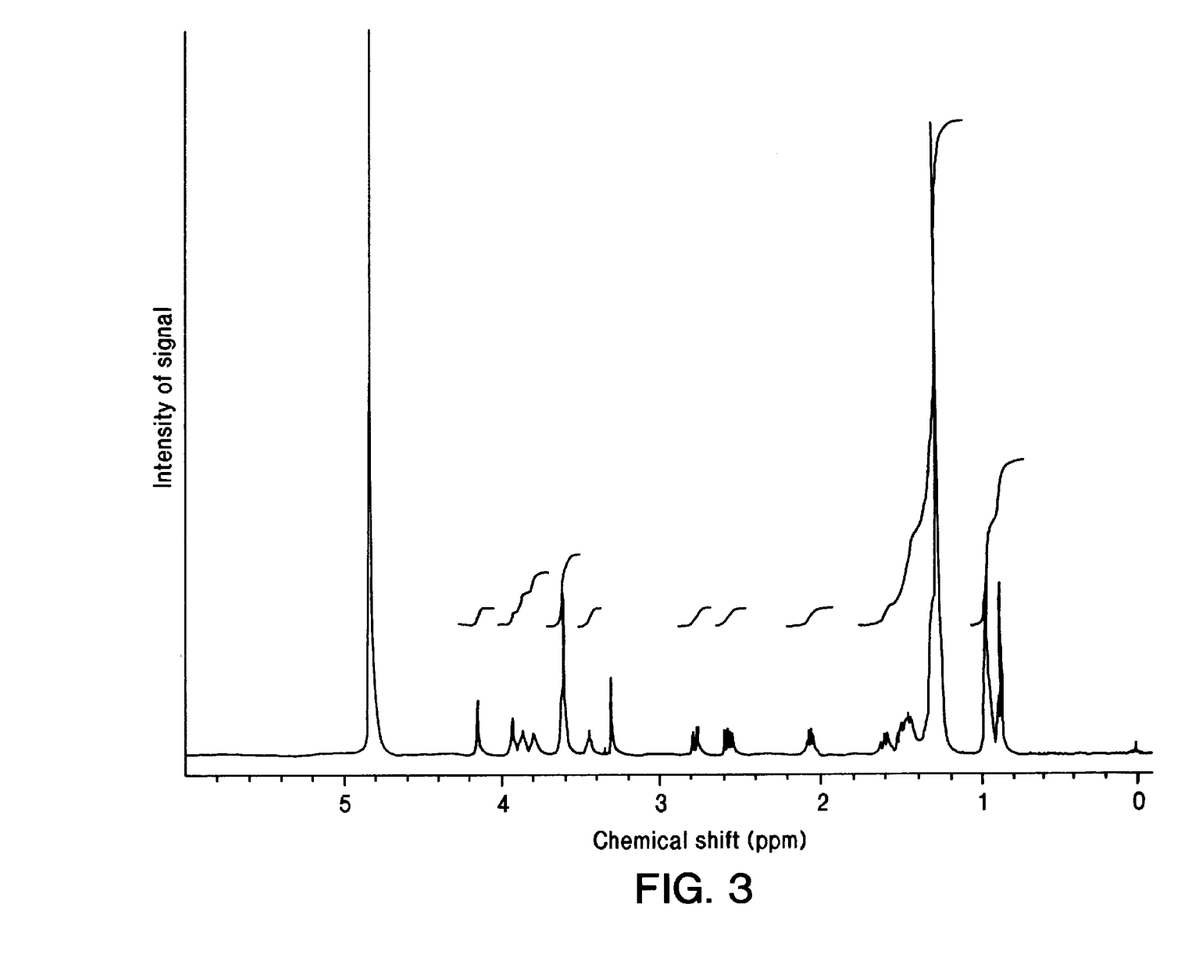
FIG. 3 is an $^1$H-NMR spectrum of the biologically active compound TKR1785-I. The ordinate represents the intensity of signal and the abscissa represents chemical shift (ppm).
Figure 4:
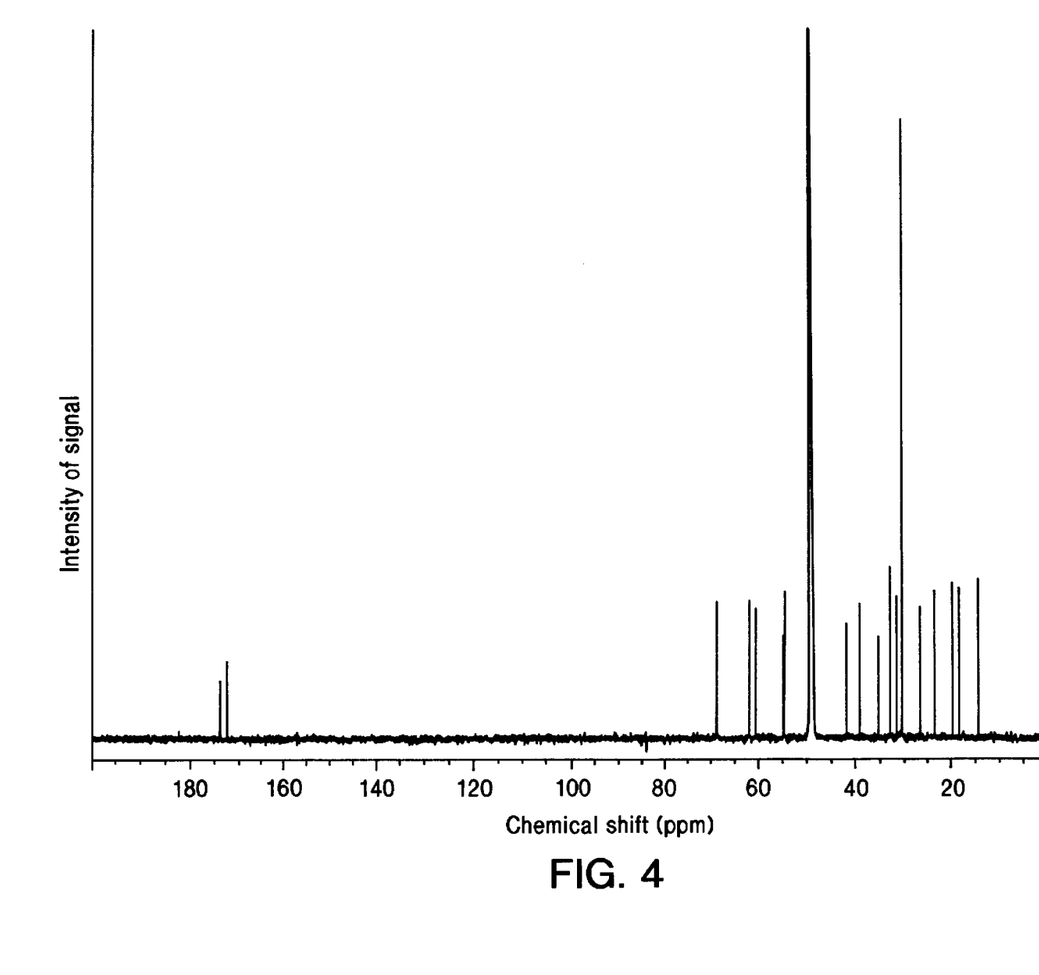
FIG. 4 is a $^{13}$C-NMR spectrum of the biologically active compound TKR1785-I. The ordinate represents the intensity of signal and the abscissa represents chemical shift (ppm).

FAB-MS of the purified white powder of fraction-I obtained by high performance liquid chromatography and concentration under reduced pressure shows m/z 518 [M+H]$^+$. Recording of $^1$H-NMR and $^{13}$C-NMR spectra and analysis thereof indicate that this substance has 27 carbon atoms and 3 nitrogen atoms. The $^1$H-NMR spectrum and $^{13}$C-NMR spectrum are presented in FIG. 3 and FIG. 4, respectively. The ultraviolet adsorption spectrum of this substance in methanol shows the terminal absorptions represented in FIG. 1. The KBr infrared absorption wave numbers (KBr) are listed below. The IR absorption spectrum of the substance is presented in FIG. 2.

Figure 2:
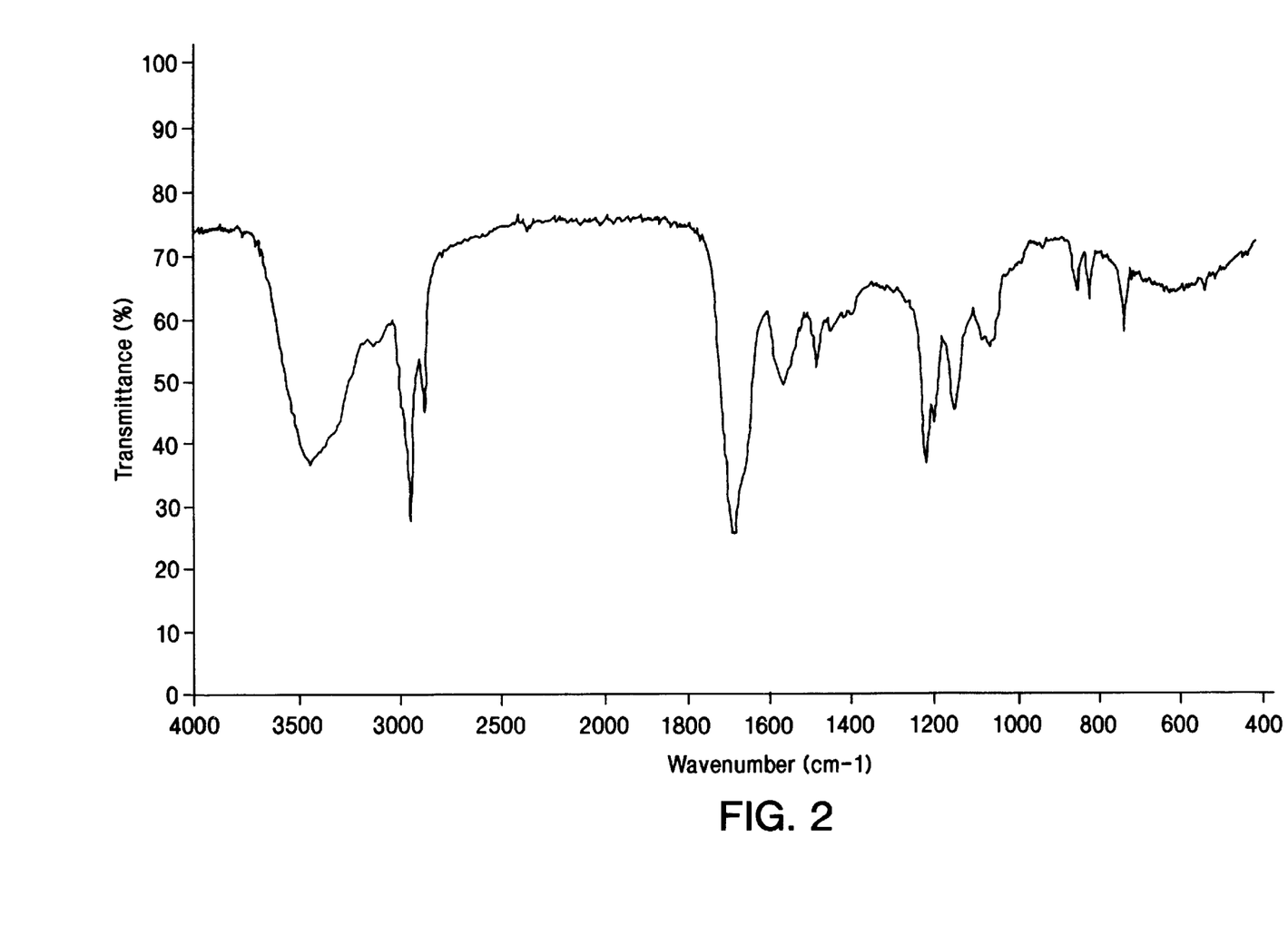
FIG. 2 is an infrared absorption spectrum of the biologically active compound TKR1785-I. The ordinate represents transmittance (%) and the abscissa represents wave number (cm$^{-1}$).

IR (KBr) (cm$^{-1}$): 3410, 2920, 2850, 1670, 1540, 1470, 1210, 1140, 1050, 840, 800, 720.

The solubility of this substance in various solvents was such that the substance is soluble in methanol and water and only sparingly soluble in chloroform and hexane.

The above analytical data revealed that the purified white powder obtained by high performance liquid chromatography and subsequent concentration of fraction I under reduced pressure is TKR1785-I. Detailed analysis of the $^1$H-NMR spectrum presented in FIG. 3 and the $^{13}$C-NMR spectrum presented in FIG. 4 revealed that TKR1785-I has the chemical structure of formula (IIa).

Figure 5:
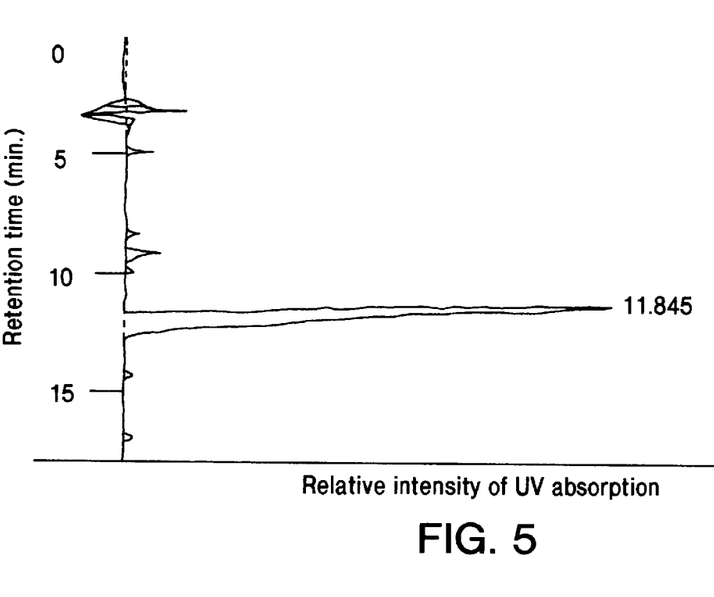
FIG. 5 shows an HPLC elution pattern of the biologically active compound TKR1785-I. The ordinate represents retention time (min.) and the abscissa represents the relative intensity of ultraviolet absorption.

TKR1785-I was subjected to reversed phase partition high performance liquid chromatography (HPLC) using LC-10A High performance Liquid Chromatography System (Shimadzu). The high performance liquid chromatography was carried out under the following conditions.
Column: CAPCELL PACK C$_{18}$ (6 mm×150 mm) (Shiseido)
Mobile phase: 0.05% trifluoroacetic acid-50% (v/v) acetonitrile/water
Column temperature: 40° C.
Detection UV wavelength: 220 nm The analysis showed that TKR1785-I is eluted in the position indicated in FIG. 5.

The physicochemical constants of TKR1785-II are as follows.

Figure 6:
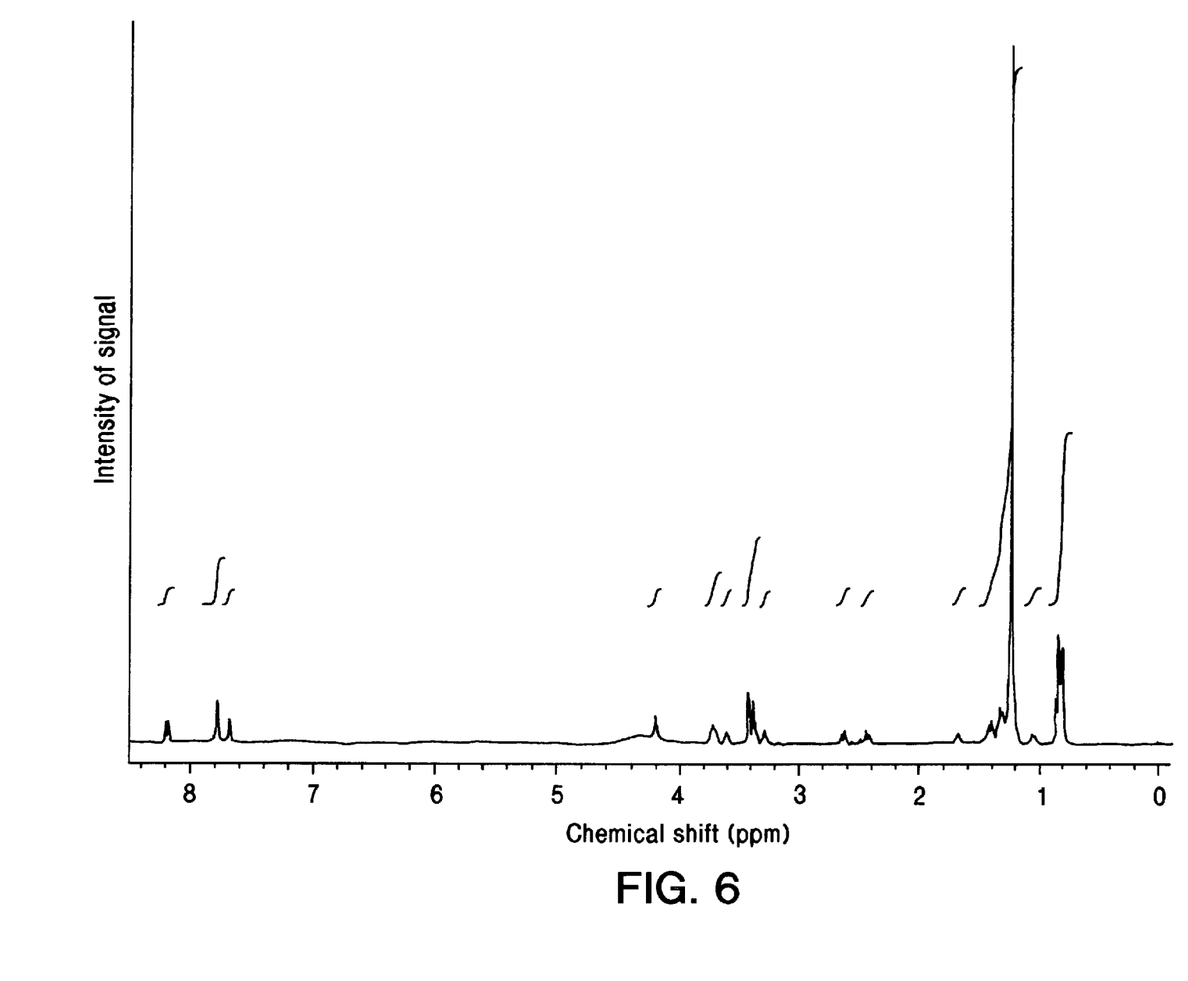
FIG. 6 is a $^1$H-NMR spectrum of the biologically active compound TKR1785-II. The ordinate represents the intensity of signal and the abscissa represents chemical shift (ppm).
Figure 7:
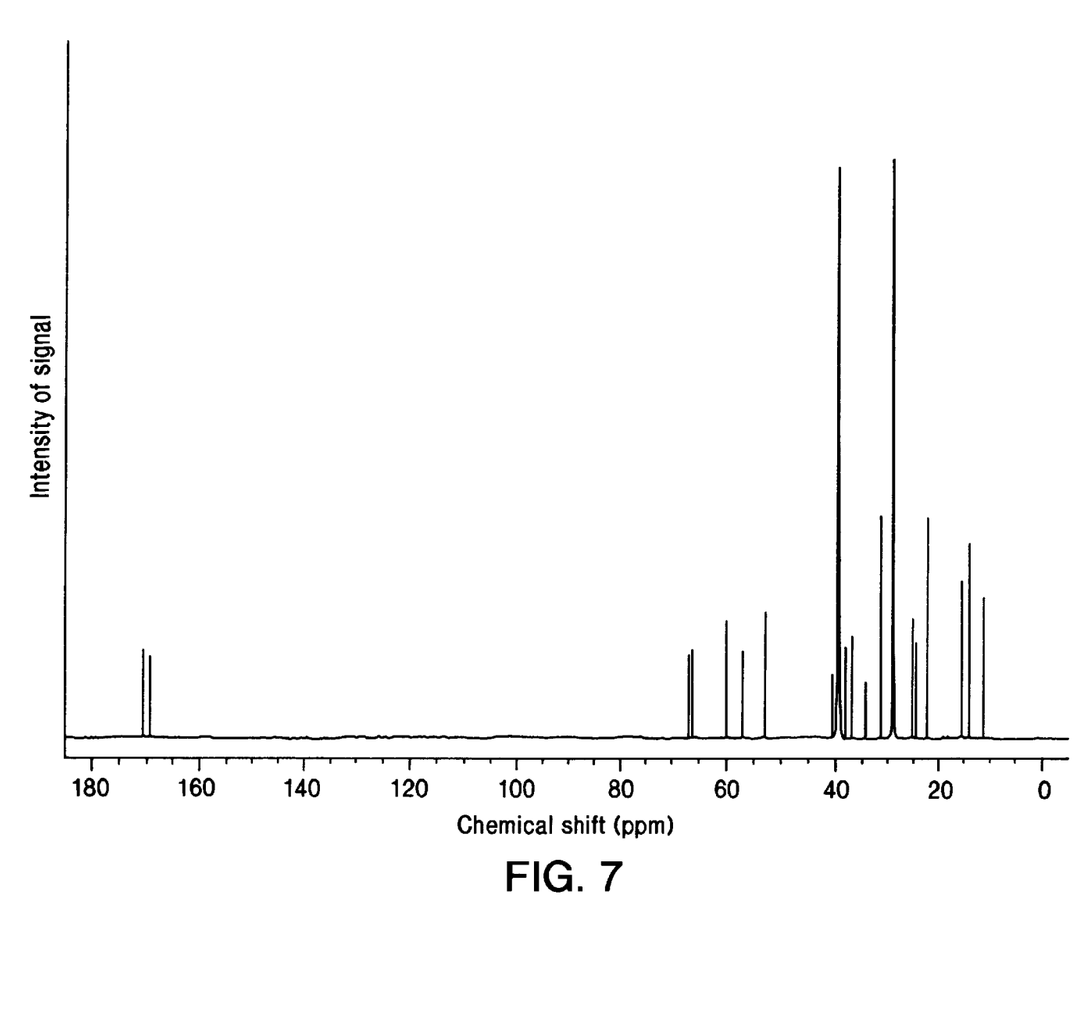
FIG. 7 is a $^{13}$C-NMR spectrum of the biologically active compound TKR1785-II. The ordinate represents the intensity of signal and the abscissa represents chemical shift (ppm).

The purified white powder obtained by high performance liquid chromatography and concentration of fraction II under reduced pressure was analyzed for various physicochemical properties. FAB-MS of this substance gave m/z532 [M+H]$^+$, indicating that it is larger than TKR1785-I by 14 mass units. This substance was hydrolyzed with hydrochloric acid and analyzed for amino acids. As a result, it was found that whereas TKR1785-I contains L-valine, this substance contains L-isoleucine. There was little difference between the UV absorption spectra of the two substances. The solubility of this substance in various solvents was also similar to that of TKR1785-I. Analysis of the $^1$H-NMR spectrum (FIG. 6) and $^{13}$C-NMR spectrum (FIG. 7) of this substance revealed that the substance has the chemical structure of formula (IIb).

Based on the above analytical data, the purified white powder obtained by high performance liquid chromatography and concentration of active fraction II under reduced pressure was found to be TKR1785-II.

Figure 8:
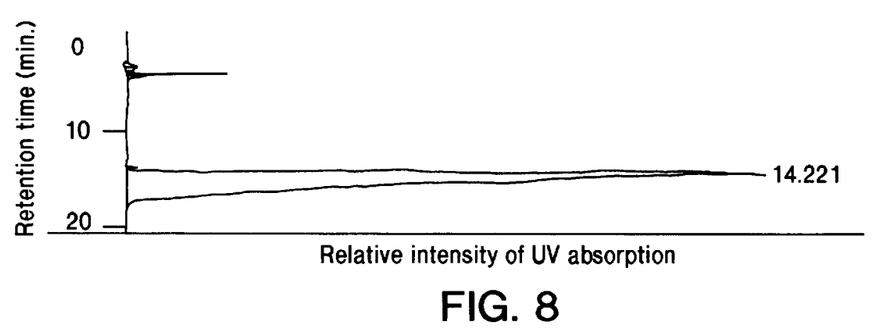
FIG. 8 shows an HPLC elution pattern of the biologically active compound TKR1785-II. The ordinate represents retention time (min.) and the abscissa represents the relative intensity of ultraviolet absorption.

TKR1785-II was subjected to HPLC analysis using LC-10A High Performance Liquid Chromatography System (Shimadzu). The HPLC conditions were the same as those used in the analysis of TKR1785-I. The analysis revealed that TKR1785-II was eluted in the position indicated in FIG. 8.

EXAMPLE 1
Synthesis of Compound (1) from TKR1785-I

To TKR1785-I (10 mg, 19.4 μmol), 6N-HCl (6 ml) wad added and the mixture was allowed to leave at 110° C. for 15 hours. The reaction mixture was neutralized by 2N-NaOH (18 ml) under ice-cooling, 6N-NaOH (4 ml) wad added thereto, and the mixture was stirred for 1 hour under ice-cooling. The reaction mixture was adjusted to pH 6.5 by 2N-HCl under ice-cooling, and concentrated under reduced pressure. Water was added to the residue, and the mixture was extracted with chloroform (total 80 ml). The chloroform extract was concentrated under reduced pressure, resulting a colorless powder (6.3 mg, 94% yield) of the compound (1) of Table 1.

FAB-MS: m/z 346 (M+H)
Thin layer chromatography (TLC) (chloroform-methanol-acetic acid-water, 8:3:1:1): Rf 0.34
UV absorption (in methanol): end absorption

EXAMPLE 2
Synthesis of the Lactone of the Compound (1) from TKR1785-I

To TKR1785-I (20 mg, 38.7 μmol), 6N-HCl (12 ml) wad added and the mixture was allowed to leave at 110° C. for 19 hours. The reaction mixture was concentrated under reduced pressure and purified by preparative thin layer chromatography (TLC) (developed and eluted with a solution of chloroform-methanol-acetic acid, 25:5:1), resulting a colorless powder (5.5 mg) of the lactone of compound (1) of Table 1.

FAB-MS: m/z 328 (M+H)
TLC (chloroform-methanol-acetic acid-water, 8:3:1:1): Rf 0.65
$^1$H-NMR (DMSO-d$_6$) δ (ppm): 4.48 (m, 1H), 3.55 (m, 1H), 3.47 (m, 1H), 2.79 (dd, 1H), 2.10 (d, 1H), 1.67 (m, 1H), 1.52 (m, 1H), 1.33 (m, 2H), 1.21 (s, 22H), 0.84 (t, 3H)
$^{13}$C-NMR (DMSO-d$_6$) δ (ppm): 176.5, 81.8, 66.7, 50.1, 38.2, 36.2, 31.3, 29.1, 29.0, 28.9, 25.1, 22,1, 13.9

EXAMPLE 3
Synthesis of Compound (2) from Compound (1)

Compound (1) (2 mg, 5.8 μmol) was dissolved in dioxane (50 μl), Boc-ON (2.2 mg, 8.7 μmol) and triethylamine (Et₃N) (1.6 μl, 11.6 μmol) were added thereto, and the mixture was stirred for 10 hours at room temperature. The reaction mixture was concentrated under reduced pressure, 10% aqueous citric acid was added thereto, and extracted with chloroform. The chloroform extract was concentrated under reduced pressure and the residue was purified by preparative TLC (developed and eluted with a solution of chloroform-methanol-acetic acid, 25:5:1), resulting a colorless powder (1 mg) of the compound (2) of Table 1.

FAB-MS: m/z 446 (M+H)

TLC (chloroform-methanol-acetic acid, 25:5:1): Rf 0.59

EXAMPLE 4
Synthesis of Compound (3)

Compound (1) (2 mg, 6.67 μmol) was dissolved in tetrahydrofuran (THF) (5.5 ml), LiAlH₄ (5 mg) was added thereto with stirring under ice-cooling. The mixture was treated with reflux for 22 hours, and cooled. Ether (2 ml), water (0.5 ml), and 1N NaOH (0.5 ml) were sucessively added thereto with stirring. The mixture was stirred for 30 min, water was added thereto, and extracted with ether (total 40 ml). The ether extract was concentrated under reduced pressure, resulting a colorless powder (2.2 mg) of the compound (3) of Table 1.

FAB-MS: m/z 332 (M+H)

1H-NMR (500 MHz, DMSO-d₆) δ: 7.75 (br), 5.26 (br), 4.77 (br), 4.37 (br), 3.74 (br), 3.61 (br), 3.52 (m), 3.02 (m), 1.74 (m), 1.62 (m), 1.50 (d), 1.44 (m), 1.35–1.23 (m), 0.84 (t)

EXAMPLE 5
Synthesis of Compound (4)

Compound (3) (10.0 mg, 30.02 μmol) was dissolved in dioxane-water (10:1, 300 μl), Boc-ON (11.5 mg, 45.3 μmol) and N,N-diisopropylethylamine (DIEA) (7.9 μl, 45.3 μmol) were added thereto, and the mixture was stirred for 6 hours. Ethyl acetate was added to the reaction mixture, and the mixture was washed with 10% aqueous citric acid and then saturated solution of sodium chloride. The ethyl acetate extract was dried on magnesium sulfate and concentrated under reduced pressure. The residue was purified by TLC (developed and eluted with a solution of chloroform-methanol, 19:1), and compound (4) of Table 1 was obtained as a colorless powder (8.5 mg).

FAB-MS: m/z 432 (M+H)

TLC (chloroform-methanol, 19:1): Rf 0.2

EXAMPLE 6
Synthesis of Compound (5)

Compound (4) (6.5 mg, 15.1 μmol) was dissolved in dichloromethane (CH₂Cl₂) (400 μl), and N,N-dimethylaminopyridine (DMAP) (1 mg), NEt₃ (2.5 μl, 18.1 μmol), and t-butyldimethylsilyl chloride (TBDMS-Cl) (2.5 mg, 16.6 μmol) were added thereto. The mixture was stirred for 16 hours at room temperature. The reaction mixture was purified by TLC (developed and eluted with a solution of chloroform-methanol, 100:1) and compound (5) of Table 1 wad obtained as a colorless oil (7.5 mg).

FAB-MS: m/z 546 (M+H)

TLC (chloroform-methanol, 100:1): Rf 0.5

EXAMPLE 7
Synthesis of Compound (6)

Compound (5) (5.0 mg, 9.16 μmol) was dissolved in CH₂Cl₂ (500 μl), and DMAP (2 mg) and Boc₂O (5.9 mg, 27.5 μmol) were added thereto. The mixture was stirred for 18 hours at room temperature. The reaction mixture was purified by TLC (developed and eluted with a solution of chloroform-methanol, 200:1) and compound (6) of Table 1 wad obtained as a colorless oil (6.0 mg).

FAB-MS: m/z 747 (M+H)

TLC [chloroform-methanol (200:1)]: Rf 0.8

EXAMPLE 8
Synthesis of Compound (7)

To compound (6) (2.5 mg, 3.35 μmol) added THF-acetic acid-water (1:2:1, 5 ml), and the mixture was stirred for 17 hours at room temperature. The reaction mixture was concentrated under reduced pressure and purified by TLC (developed and eluted with a solution of chloroform-methanol, 50:1), resulting a colorless oil (1.8 mg) of compound (7) of Table 1.

FAB-MS: m/z 632 (M+H)

TLC [chloroform-methanol (50:1)]: Rf 0.4

EXAMPLE 9
Synthesis of Compound (8)

Compound (1) (5 mg, 14.5 μmol) was suspended in acetone (900 μl), acetone dimethyl acetal (150 μl) and dl-camphor sulfonic acid (1 mg) were added thereto, and the mixture was stirred for 1 hour at room temperature. The reaction mixture was neutralized with NEt₃ (10 μl) and concentrated under reduced pressure. The residue was purified by TLC [the lower layer of a mixture of chloroform-methanol-water (8:3:1)], and compound (8) of the Table 1 was obtained as a colorless oil (2.8 mg, yield 51%).

FAB-MS: m/z 386 (M+H)

TLC [the lower layer of chloroform-methanol-water (8:3:1)]: Rf 0.4

EXAMPLE 10
Synthesis of Compound (9)

Compound (8) (1.4 mg, 3.6 μmol) was dissolved in pyridine (100 μl), trichloroethoxycarbonyl chloride (1.5 μl, 10.9 μmol) was added thereto. The mixture was stirred for 30 min under ice-cooling and stirred for 1 hour at room temperature. The reaction mixture was purified by TLC (the lower layer of a mixture of chloroform-methanol-water, 8:3:1), and compound (9) of the Table 1 was obtained as a colorless powder (1.0 mg, yield 42%)

FAB-MS: m/z 734 (M+H)

TLC [the lower layer of chloroform-methanol-water (8:3:1)]: Rf 0.6

TABLE 1

$$H_3C-(CH_2)_{12}-\overset{Q^5}{\underset{|}{CH}}-\overset{Q^4}{\underset{|}{CH}}-\overset{OQ^3}{\underset{|}{CH}}-\overset{N(Q^2)-Q^1}{\underset{|}{CH}}-CH_2-X^1 \quad (I)$$

| | | $Q^5$ | $Q^4$ | $Q^3$ | $Q^2$ | $Q^1$ | $X^1$ |
|---|---|---|---|---|---|---|---|
| Compound | (1) | OH | H | H | H | H | COOH |
| | (2) | OH | H | H | H | Boc | COOH |
| | (3) | OH | H | H | H | H | CH₂OH |
| | (4) | OH | H | H | H | Boc | CH₂OH |
| | (5) | OH | H | H | H | Boc | CH₂OTBDMS |
| | (6) | OBoc | H | Boc | H | Boc | CH₂OTBDMS |
| | (7) | OBoc | H | Boc | H | Boc | CH₂OH |
| | (8) | OH | H | isopropylidene | | H | COOH |
| | (9) | OH | H | isopropylidene | | Troc | COOH |
| | (10) | — (double bond) | — | H | H | H | COOH |
| | (11) | — (double bond) | — | H | H | H | CH₂OH |

REFERENCE EXAMPLE 2
Synthesis of TKR1785-I

TKR1785-I was synthesized according to the method shown in Scheme 1. That is, Boc-NH—CH(CH$_2$OH)—CH$_2$OBzl was used as the starting material to prepare HCl·H$_2$N—CH(CH(CH$_3$)$_2$)—CO—NH—CH(CH$_2$OAc)—CH$_2$OBzl. This compound (3.0 mg) was coupled with compound (9) (3.0 mg), resulting a protected derivative of TKR1785-I (3.9 mg). Removal of the protecting group of the compound by a conventional method gave TKR1785-I as a white powder (1.2 mg).

FAB-MS: m/z 518 (M+H)

The final product obtained was analyzed by reversed phase high performance chromatography (HPLC) to compare with TKR1785-I obtained by purification of a cultured broth. The condition of HPLC is as follows.

Column: CAPCELL PACK C$_{18}$ (6 mm×150 mm) (manufactured by Shiseido)

Mobile phase: 50% (v/v) acetonitril/water containing 0.05% trifluoro acetic acid Column temperature: 40° C.

UV wave-length for detection: 220 nm

As a result, the product obtained by synthesis and the natural product were eluted at the identical position.

In addition, the final product obtained was dissolved in methanol at the concentration of 1 mg/ml, tested for the antimicrobial activity against *C. albicans TIMM* 0136 using the medium composed of yeast nitrogen base (Difco) 0.67%, glucose 1%, and agar 1.5% by paper disk diffusion method (20 μl/disk of 6 mm in diameter), and showed a prominent growth inhibitory activity.

These results indicated that the compound prepared by the chemical synthesis was identical to TKR1785-I. That is, it has found that compound (1) is useful as the intermediate for synthesis of TKR1785-I.

TABLE 2

(scheme 1)

[Scheme 1 showing multi-step synthesis starting from H$_3$C—(CH$_2$)$_{12}$—CH(OH)—CH$_2$—CH(OH)—CH(NH$_2$)—CH$_2$—COOH (1) and Boc-NH—CH(CH$_2$OH)—CH$_2$OBzl, through sequential reactions: Boc-ON, Et$_3$N; Ac$_2$O, pyridine; Ac$_2$O, pyridine; HCl/dioxane solution; Boc-NH—CH(CH(CH$_3$)$_2$)—COOH, DCC, HOBt; HCl/dioxane solution; DIPCDI, HOAt; H$_2$/Pd-black; 1N NaOH/methanol; TFA; to give TKR1785-I: H$_3$C—(CH$_2$)$_{12}$—CH(OH)—CH$_2$—CH(OH)—CH(NH$_2$)—CH$_2$—CONH—CH(CH(CH$_3$)$_2$)—CONH—CH(CH$_2$OH)—CH$_2$OH]

INDUSTRIAL APPLICABILITY

The present invention provides a novel lipid, which is useful as an intermediate for syntheses of TKR1785's and their derivatives useful as drugs for the treatment of fungal infections, allergic diseases, etc., and also as an intermediate for syntheses of novel sphingolipid derivatives, and a process thereof.

What is claimed is:

1. A sphingosine analogue represented by the following general formula (I):

(I)

In the formula, as for Q$^1$, Q$^2$ and Q$^3$, Q$^1$ and Q$^2$, which are the same or different each other, are hydrogen, alkyl groups having 1–4 of carbon atoms, acyl groups having 2–5 of carbon atoms, or protecting groups of the amino group, and $Q^3$ is a hydrogen or a protecting group of the hydroxyl group; or $Q^2$ and $Q^3$ make up an isopropylidene group and $Q^1$ is a hydrogen or a protecting group of the amino group, $Q^4$ and $Q^5$, which are the same or different each other, are hydroxyl groups, acyl groups having 2–5 of carbon atoms, —O—$Q^6$, or hydrogen; or $Q^4$ and $Q^5$ make up a covalent bond, $Q^6$ is a protecting group of the hydroxyl group, $X^1$ is —COOH, —CONH$_2$, —CO—$Q^7$, —CH$_2$OH, or —CH$_2$O—$Q^8$, $Q^7$ is a protecting group of the carboxyl group, and $Q^8$ is a protecting group of the hydroxyl group.

* * * * *